United States Patent
Winter et al.

(10) Patent No.: US 9,301,959 B2
(45) Date of Patent: Apr. 5, 2016

(54) ORALLY DISPERSIBLE TABLET CONTAINING COMPACTED SILDENAFIL BASE

(71) Applicant: RATIOPHARM GMBH, Ulm (DE)

(72) Inventors: Sven Winter, Neubeckum (DE); Max-Werner Scheiwe, Maulburg (DE); Dieter Swatschek, Blaubeuren (DE)

(73) Assignee: ratiopharm GmbH, Ulm (DE)

( * ) Notice: Subject to any disclaimer, the term of this patent is extended or adjusted under 35 U.S.C. 154(b) by 63 days.

(21) Appl. No.: 14/452,209

(22) Filed: Aug. 5, 2014

(65) Prior Publication Data

US 2014/0343072 A1    Nov. 20, 2014

Related U.S. Application Data

(63) Continuation of application No. 13/515,515, filed as application No. PCT/EP2010/007891 on Dec. 22, 2010, now Pat. No. 8,808,739.

(51) Int. Cl.
| | |
|---|---|
| *A61K 31/519* | (2006.01) |
| *A61K 9/20* | (2006.01) |
| *A61K 9/00* | (2006.01) |
| *A61K 9/16* | (2006.01) |

(52) U.S. Cl.
CPC ............ *A61K 31/519* (2013.01); *A61K 9/0056* (2013.01); *A61K 9/1652* (2013.01); *A61K 9/2009* (2013.01); *A61K 9/2013* (2013.01); *A61K 9/2027* (2013.01); *A61K 9/2054* (2013.01); *A61K 9/2059* (2013.01); *A61K 9/2077* (2013.01); *A61K 9/2095* (2013.01)

(58) Field of Classification Search
CPC .. A61K 31/519; A61K 9/0056; A61K 9/2054
See application file for complete search history.

(56) References Cited

U.S. PATENT DOCUMENTS

| | | | |
|---|---|---|---|
| 6,221,402 B1* | 4/2001 | Itoh ................... | A61K 9/5073 424/490 |
| 6,743,443 B1* | 6/2004 | Furitsu ............... | A61K 9/0056 424/435 |
| 2002/0001617 A1* | 1/2002 | Lee ..................... | A61K 9/0056 424/465 |
| 2002/0002172 A1* | 1/2002 | Bell-Huff ............ | A61K 9/0056 514/252.16 |
| 2002/0004498 A1* | 1/2002 | Doherty, Jr. ......... | A61K 9/0031 514/182 |
| 2006/0100214 A1* | 5/2006 | Tian ..................... | A61K 9/1617 514/252.16 |

FOREIGN PATENT DOCUMENTS

IN    WO 03086343 A2 * 10/2003  ........... A61K 9/0056

* cited by examiner

*Primary Examiner* — Bethany Barham
*Assistant Examiner* — Peter Anthopolos
(74) *Attorney, Agent, or Firm* — Milstein Zhang & Wu LLC

(57) ABSTRACT

The invention relates to a process for the preparation of a pharmaceutical intermediate, comprising the steps of (i) mixing (a-i) sildenafil base, (b-i) wicking agent, (c-i) disintegrant, (d-i) optionally glidant; (ii) compacting the mixture; and (iii) milling the compacted material; and to an intermediate obtainable by that process. In addition, the invention relates to a process for the preparation of an orally dispersible tablet (hereinafter also referred to as an "orodispersible tablet") comprising the intermediate of the invention, and to orodispersible tablets obtainable by that process.

19 Claims, No Drawings

ORALLY DISPERSIBLE TABLET CONTAINING COMPACTED SILDENAFIL BASE

The invention relates to a process for the preparation of a pharmaceutical intermediate, comprising the steps of (i) mixing (a-i) sildenafil base, (b-i) wicking agent, (c-i) disintegrant, (d-i) optionally glidant; (ii) compacting the mixture; and (iii) milling the compacted material; and to an intermediate obtainable by that process. In addition, the invention relates to a process for the preparation of an orally dispersible tablet (hereinafter also referred to as an "orodispersible tablet") comprising the intermediate of the invention, and to orodispersible tablets obtainable by that process.

The IUPAC name of sildenafil [INN] is 1-{[3-(1-methyl-7-oxo-3-propyl-6,7-dihydro-1H-pyrazolo-[4,3-d]pyrimidine-5-yl)-4-ethoxyphenyl]-sulphonyl}-4-methyl piperazine. The chemical structure of sildenafil is shown in formula (1) below:

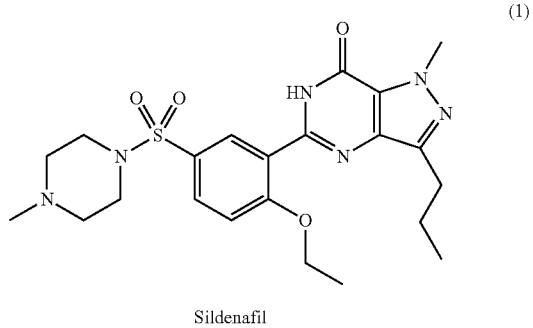 [SMILES: CCCc1nn(C)c2c(=O)[nH]c(-c3cc(S(=O)(=O)N4CCN(C)CC4)ccc3OCC)nc12]

Sildenafil (1)

Sildenafil is a potent selective inhibitor of type 5 cGMP-specific phosphodiesterase (PDE-5), which is responsible for the reduction of cGMP in the Corpus cavernosum. Sildenafil in the form of its citrate salt is marketed under the trade name Viagra® for the treatment of erectile dysfunction.

Various processes for the preparation of an orodispersible tablet containing sildenafil are proposed in the state of the art. EP 0 960 621 A2 describes the preparation of porous orodispersible tablets containing sildenafil, wherein a water-soluble, meltable binder, at least one excipient and sildenafil are first shaped into a tablet, after which the binder is melted and solidified.

EP 1 120 120 A1 describes a process for the preparation of an orodispersible tablet, which comprises mixing a cyclic GMP phosphodiesterase inhibitor with a saccharide, kneading that mixture with an organic solvent, water or an aqueous organic solvent and then compressing it in a mould to form an orodispersible tablet.

WO 2009/123626 describes orally dispersible tablets with PDE-5 inhibitors, wherein up to 50% by weight of cation exchange resin is required for formulation purposes, which can have a negative effect on the feeling in the mouth. Furthermore, the sildenafil formulations described are complex to prepare, since two wet granulation steps are needed (1. wet granulation: sildenafil+cation exchange resin, 2. wet granulation: excipients).

The processes described in the state of the art for the preparation of orodispersible tablets are complex and only make it possible to obtain orodispersible tablets with a content of active agent of well under 50% by weight. However, if the dosage remains unchanged, such a low content of active agent leads to a higher tablet weight, which can often cause problems with regard to the tablet properties. Orodispersible tablets with too high a tablet weight (e.g. more than 300 mg) are often rejected by patients, because after the orodispersible tablet has disintegrated, there is a large amount of tableting mixture in the buccal cavity, which is felt to be disturbing and unpleasant. The disintegration time and the feeling caused in the mouth by the tablets obtainable in the state of the art are in need of improvement. A drug load of more than 45% or even more than 50% cannot be advantageously achieved with the processes described, in particular not with an advantageous disintegration time and a pleasant feeling in the mouth. In addition, it has been found that it is not possibly simply to increase the drug load with the process known in the state of the art, also with regard to the physical parameters, since reducing the proportion of excipients leads to disadvantageous tablet properties (e.g. in terms of hardness and friability).

In addition, it has been found that the disintegration time of the orodispersible tablets described in the state of the art increases undesirably after lengthy storage.

To sum up, it can be stated that the formulations proposed in the state of the art involve disadvantages. The objective of the invention was therefore to overcome those disadvantages.

Specifically, it was an object of the present invention to provide an orodispersible tablet containing sildenafil which can have a drug load of more than 50% by weight.

In addition, it was an object of the invention to provide an orodispersible tablet which, after the patient has taken it, is felt not to be disturbing and not unpleasant in terms of taste and the feeling in the mouth.

In addition, it was an object of the invention to provide an oral dosage form that achieves a good feeling in the mouth and a good taste for the patient (i.e. the patient should not experience an unpleasant—e.g. bitter—taste, and the mass of tablet material should not be so great per se that it is felt to be unpleasant).

The expression "feeling in the mouth" as used herein describes the physical and chemical interactions of a substance or mixture of substances (in the present case especially the orodispersible tablet of the invention) in the mouth. It includes the impressions from the first contact with the palate, chewing and swallowing and the aftertaste.

The feeling in the mouth can be described on the basis of the following criteria, for example ("sample" means a characteristic composition, formulation or pharmaceutical final dosage form containing active agent and excipient or excipients):

mouth lining: nature and degree of the coating on teeth and mucous membrane of the buccal cavity. It is usually relevant to consider the lining after the sample has been chewed or has disintegrated, i.e. immediately before swallowing;

density: density of the cut surface in the sense of the density of the packing, i.e. layering or continuous compressed material or granules or the like comprising or consisting of, for example, the mixture according to a formulation, after a sample or, as described, a product or a final dosage form has been completely severed with the molars;

elasticity: ability of the sample (or the product or the final dosage form) to return to its original shape after being exposed to a force;

hardness: measure of the force subjectively felt to be required in order to deform the sample by a defined amount, or to break it;

moisture: amount or effect of a given amount of liquid perceived as such on the surface of the sample;

moisture absorption: amount of saliva absorbed by the sample;

uniformity: describes the uniformity of a sample (taste, texture, colour etc.);

granularity: degree of graininess felt during the chewing process;

adhesion: the force required to remove the material to be tested from a particular surface (lips, teeth, palate etc.);

roughness: degree of sensed abraded matter left behind on the tongue by the sample;

smoothness: degree to which the sample slides over the tongue;

heaviness: weight of the sample sensed upon its first contact with the tongue;

crushability: the force required to make the sample disintegrate.

In addition, it was an object of the invention to provide an orodispersible tablet that exhibits rapid disintegration in the mouth and even after lengthy storage still satisfies the requirements of rapid disintegration and not only possesses the general requirements expected of pharmaceutical products, such as the stability of the active agent, but also avoids any discoloration or decomposition or other undesirable changes of a physical, chemical or physico-chemical nature.

"Rapid disintegration" in the context of this invention means a disintegration time, determined in accordance with Ph. Eur. 6.0, section 2.9.1 Test A, of less than 100 seconds, preferably less than 50 seconds, even more preferably less than 30 seconds, in particular less than 25 seconds.

In addition, the intention is to provide orodispersible tablets which exhibit both advantageous friability and advantageous hardness.

It was possible to solve the problems by means of a process for the preparation of an orodispersible tablet containing sildenafil base, wicking agent and disintegrant, especially by employing a compacting step.

The subject matter of the invention is therefore a process for the preparation of a pharmaceutical intermediate, comprising the steps of (i) mixing
 (a-i) sildenafil base,
 (b-i) wicking agent,
 (c-i) disintegrant,
 (d-i) optionally glidant;
(ii) compacting the mixture; and
(iii) milling the compacted material.

A further subject matter of the invention is a process for the preparation of an orodispersible tablet containing sildenafil base, comprising the steps of (I) preparing the intermediate of the invention,
(II) mixing the intermediate with further pharmaceutical excipients, and
(III) compressing the mixture from step (II) into an orodispersible tablet.

The processes for the preparation of the intermediate of the invention and the orodispersible tablet of the invention can thus be combined. The invention therefore also relates to a process for the preparation of an orodispersible tablet containing sildenafil base, comprising the steps of (I) preparing an intermediate, comprising the steps of
 (i) mixing
  (a-i) sildenafil base,
  (b-i) wicking agent,
  (c-i) disintegrant,
  (d-i) optionally glidant,
 (ii) compacting the mixture, and
 (iii) milling the compacted material, (II) mixing the intermediate with further pharmaceutical excipients, and
(III) compressing the mixture from step (II) into an orodispersible tablet.

In addition, a subject matter of the invention is an intermediate obtainable by the process of the invention and an orodispersible tablet obtainable by the process of the invention.

A further subject matter of the invention is an orodispersible tablet containing 45 to 70% by weight sildenafil base,
10 to 35% by weight wicking agent, in particular microcrystalline cellulose,
5 to 20% by weight disintegrant, in particular crospovidone,
0 to 5% by weight glidant, in particular silicon dioxide,
0 to 10% by weight lubricant, in particular sodium stearyl fumarate or magnesium stearate.

Finally, a subject matter of the invention is the use of sildenafil base in particulate form, wherein the D50 value of the particle size distribution is 10 to 55 µm, preferably 20 to 45 µm, and the D90 value of the particle size distribution is 60 to 250 µm, preferably 100 to 200 µm, for the preparation of an orodispersible tablet, preferably for the preparation of an orodispersible tablet with a hardness of 30 to 90 N and a friability of less than 1%, preferably 0.01 to 0.5%. In an alternative preferred embodiment, a subject matter of the invention is the use of sildenafil base in particulate form, wherein the D50 value of the particle size distribution is 1 to 25 µm, preferably 2 to 15 µm, and the D90 value of the particle size distribution is 5 to 80 µm, preferably 10 to 55 µm, for the preparation of an orodispersible tablet, preferably for the preparation of an orodispersible tablet with a hardness of 30 to 90 N and a friability of less than 1%, preferably 0.01 to 0.5%.

The particle size distribution is preferably determined, as explained in more detail below, with a laser diffraction measuring unit, which is known per se and is applied to perform a dry measurement. The details regarding D10, D50 and D90 etc. relate here to the total throughput curve, weighted with a calculated representative diameter or volume of the particles; hence, D10 is the particle size at which 10% are smaller than the D value stated, D50 means 50% are smaller, and D90 that 90% are smaller than the D value stated.

As explained above, the present invention relates to a process for the preparation of a pharmaceutical intermediate.

According to the present invention, an "intermediate" is usually understood to mean a pharmaceutical composition which is not administered directly, but is instead converted into an applicable oral dosage form by means of suitable processes, such as granulation and/or compression.

The process of the invention for the preparation of the pharmaceutical intermediate comprises the steps of (i) mixing, (ii) compacting the mixture and (iii) milling the compacted material.

"Mixing" is understood in the context of the invention as meaning a process for combining substances with the aim of achieving a substantially homogeneous distribution of different substances by the action of mechanical forces. Mixing for the purposes of the invention is performed in conventional mixing devices, such as asymmetric moved mixers, roll mixers, shaking mixers, free-fall mixers, shear mixers, ploughshare mixers, planetary mixing kneaders, Z or sigma kneaders or fluid or intensive mixers. It is preferable to use an asymmetric moved mixer.

The mixing time in step (i) is usually 1 to 30 minutes, preferably 2 minutes to 20 minutes, more preferably 5 minutes to 17 minutes.

As already mentioned, step (i) of the process of the invention comprises mixing the components (a-i) sildenafil base, (b-i) wicking agent, (c-i) disintegrant, (d-i) optionally glidant and optionally further pharmaceutical excipients.

Especially in the preparation of larger batches, it has proven advantageous if, in the preparation of the intermediate of the invention, the wicking agent (b-i) and the glidant (d-i) are premixed. Hence, it is preferable that in step (i), a premixed mixture of wicking agent and glidant is used. Similarly, in the premixing step described, sweeteners and/or flavourings can be premixed as well. It is particularly preferable for the premixing to be performed by premixing for 5 to 30 minutes. By premixing the wicking agent and glidant, it was in particular possible to exert a positive influence on the uniformity of the content.

In the context of this invention, component (a-i) sildenafil base is understood to mean 1-{[3-(1-methyl-7-oxo-3-propyl-6,7-dihydro-1H-pyrazolo-[4,3-d]pyrimidine-5-yl)-4-ethoxyphenyl]-sulphonyl}-4-methyl piperazine in accordance with formula (1) above. The compound of formula (1) is present here in the form of the free base and not in salt form.

Component (a-i) sildenafil base is usually employed in step (i) in an amount of 40 to 98% by weight, preferably 55 to 95% by weight, in particular 60 to 90% by weight, based on the total weight of the intermediate.

In general, component (b-i) wicking agent is a substance with the ability to draw up a biological fluid (preferably water) into a solid (preferably in the orodispersible tablet of the invention or in the intermediate of the invention, preferably by means of physisorption). Physisorption is defined as a form of adsorption in which the liquid molecules can adhere to the surface of the wicking agent, preferably by means of van der Waals binding between the surface of the wicking agent and the adsorbed fluid molecule (preferably water). Normally a wicking agent achieves this with or without swelling. Normally, a non-swelling wicking agent which attracts water will ultimately have a volume consisting substantially of the volume of the wicking agent and the amount of water which it attracts. In general, a swelling wicking agent will have a volume consisting substantially of the volume of the wicking agent, the volume of the water which it attracts, and an additional volume, caused by steric and molecular forces acting between the cellulose chains and water molecules deposited on them. It is preferable to use non-swelling wicking agents or wicking agents whose swelling behaviour in relation to the water transport behaviour is of minor importance for the effect of the invention described in the following.

In the intermediate of the invention or in the tablet of the invention, the wicking agent (b-i) preferably causes the formation of channels or pores. This facilitates the penetration of the water molecules into the orodispersible tablet, especially by physisorption. The function of the wicking agent therefore consists in transporting water to the surfaces inside the intermediates in order in this way to create channels in or a network on an enlarged surface.

Examples of wicking agents used are: microcrystalline cellulose, silicified microcrystalline cellulose, kaolin, titanium dioxide, fumed silica, aluminium, niacinamide, M-pyrol, bentonite, magnesium-aluminium silicate, polyester, polyethylene, or mixtures thereof. The wicking agents of the pharmaceutical composition of the present invention preferably contain cellulose and cellulose derivatives, such as silicified microcrystalline cellulose, and mixtures thereof. Microcrystalline cellulose is particularly preferably used as a wicking agent. It is commercially available, under the trade name Avicel® for example. In the context of this invention, microcrystalline cellulose with a weight-average molecular weight of 10,000 to 70,000 g/mol, preferably 25,000 to 45,000 g/mol, more preferably 30,000 to 40,000 g/mol is usually employed. The weight-average molecular weight is usually determined by means of gel permeation chromatography in this context.

It is preferable here that a microcrystalline cellulose is usually employed which is prepared from native alpha-cellulose by complete or preferably partial acid hydrolysis. In the context of this invention, microcrystalline cellulose with a water content of <1.5% by weight, preferably 0.01 to 1.2% by weight, is usually employed. In the context of this application, the water content is preferably determined with a Mettler Toledo HR83 halogen moisture apparatus at 80° C. and 6 min. measuring time. Usually, a sample weighing 3.0 g is analysed.

Component (b-i) wicking agent is usually employed in step (i) in an amount of 1 to 40% by weight, more preferably 5 to 35% by weight, in particular 10 to 30% by weight, based on the total weight of the orodispersible tablet.

Component (c-i) disintegrant is the term generally used for one or more substances which accelerate the disintegration of a dosage form, especially a tablet, after it is placed in water. Suitable disintegrants are, for example, organic disintegrants such as carrageenan, celluloses and cellulose derivatives, croscarmellose, starches and starch derivatives, sodium carboxymethyl starch, polysaccharides, soya polysaccharides, alginates and crospovidone. Alkaline disintegrants can likewise be used. The term "alkaline disintegrants" means disintegrants which, when dissolved in water, produce a pH level of more than 7.0. Mixtures of the above-mentioned disintegrants may also be used.

Crospovidone is preferably used as the disintegrant. In the context of this invention, crospovidone is usually understood to mean a cross-linked homopolymer of N-vinyl-2-pyrrolidone, which is also referred to as cross-linked polyvinyl polypyrrolidone (PVPP). Crospovidone can generally be prepared in accordance with U.S. Pat. No. 2,938,017 and usually has a weight-average molecular weight of more than 1,000,000 g/mol.

Component (c-i) disintegrant is usually employed in step (i) in an amount of 1 to 30% by weight, more preferably 2 to 15% by weight, especially 5 to 12% by weight, based on the total weight of the orodispersible tablet.

In principle, it would also be possible to use a copolymer obtainable by the copolymerisation of methacrylic acid and divinyl benzene as disintegrant (c-i). A copolymer of this kind is known under the name of polacrilin, especially in the form of the potassium salt (polacrilin potassium, especially as monographed in accordance with the US Pharmacopoeia).

Polacrilin potassium can be illustrated by the following structural formula.

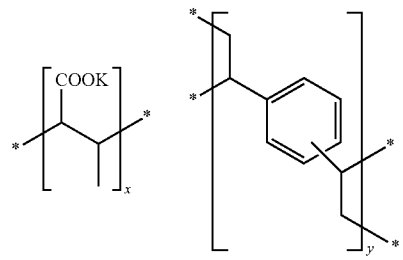

where x and y are natural numbers, such as $10^1$ to $10^{20}$, preferably $10^6$ to $10^{18}$. The ratio of x to y is usually 50:1 to 1:1, preferably 20:1 to 2:1, particularly preferably 10:1 to 3:1.

The use of polacrilin potassium (e.g. in amounts of 50% by weight) may, however, have a negative effect on the feeling in the mouth. In a preferred embodiment, the orodispersible tablet of the invention therefore contains less than 10% by weight polacrilin potassium, particularly preferably less than 5% by weight polacrilin potassium, in particular no (i.e. 0% by weight) polacrilin potassium.

Component (d-i) glidant usually means substances which serve to improve powder flowability. The task of glidants is to reduce both the interparticular friction (cohesion) between the individual particles in a tableting mixture and their adherence to the wall surfaces of the press mould (adhesion). One example of an additive to improve powder flowability is disperse silicon dioxide (e.g. obtainable as Aerosil®). Preferably, silicon dioxide is used with a specific surface area of 50 to 400 m$^2$/g, determined by gas adsorption in accordance with Ph. Eur., 6th edition 2.9.26.

Component (d-i) glidant is usually employed in step (i) in an amount of 0 to 10% by weight, more preferably 0.1 to 5% by weight, especially 0.5 to 3% by weight, based on the total weight of the intermediate.

In addition, in a preferred embodiment, the sweeteners and/or flavourings explained in more detail below may be added in step (i).

It has unexpectedly been found that in order to solve the problems described at the beginning, it is particularly advantageous if in step (i) of the process of the invention the substances used are present with a specific particle size distribution. Especially with regard to the feeling in the mouth and the physical characteristics of a resulting orodispersible tablet, the particle size distribution can be important, it being necessary to take into account both the D50 value (in particular for the feeling in the mouth) and also the D90 value (in particular for physical characteristics such as hardness and friability).

In a preferred embodiment, particulate sildenafil base is therefore used as component (a-i) in which the D50 value of the particle size distribution of the particulate sildenafil base is 1 to 25 μm, more preferably 2 to 15 μm. The D90 value of the particle size distribution of the particulate sildenafil base is preferably 5 to 80 μm, more preferably 10 to 55 μm. The D10 value of the particle size distribution of the particulate sildenafil base is preferably 0.1 to 5 μm, more preferably 1.0 to 4.0 μm.

In a further preferred embodiment (both in the preparation of the intermediate of the invention and in the preparation of the orodispersible tablet of the invention), the wicking agent (b) and/or the disintegrant (c) are used in particulate form, in which the D50 value of the particle size distribution is 20 to 120 μm, more preferably 50 to 110 μm. The D90 value of the particle size distribution of the wicking agent and/or disintegrant is preferably 100 to 300 μm, more preferably 125 to 250 μm.

In a further preferred embodiment, the ratio between the D90 value and D50 value (=D90/D50) of sildenafil base, wicking agent and/or disintegrant has a value of between 1.1 and 25, preferably between 2.0 and 8.0, particularly preferably between 2.5 and 6.0.

In a further preferred embodiment, the ratio between the D50 value and D10 value (=D50/D10) of sildenafil base, wicking agent and/or disintegrant has a value of between 2 and 550, preferably between 5 and 45, particularly preferably between 8 and 12.

In a further preferred embodiment, the ratio between the D90 value and D10 value (=D90/D10) of sildenafil base, wicking agent and/or disintegrant has a value of between 12 and 2,500, preferably between 25 and 200, particularly preferably between 40 and 60.

The "particle size" is determined in the context of this invention by means of laser diffractometry. In particular, a Malvern Instruments Mastersizer 2000 is used to determine the diameter (dry measurement at 20° C., dispersed in air), the evaluation being performed according to the Fraunhofer model). The average particle diameter (=the average particle size), which is also referred to as the D50 value of the integral volume distribution, is defined in the context of this invention as the particle diameter at which 50% by volume of the particles have a smaller diameter than the diameter which corresponds to the D50 value. Similarly, 50% by volume of the particles then have a larger diameter than the D50 value. The D90 value of the particle size distribution is accordingly defined as the particle size at which 90% by volume of the particles have a smaller particle size than the particle size corresponding to the D90 value. Analogously, the D10 value of the particle size distribution of the intermediate is defined as the particle size at which 10% by volume of the particles have a smaller particle size than the particle size corresponding to the D10 value.

In a further preferred embodiment of the process of the invention, the ratio of the weight of component (a-i) to the combined weight of components (b-i) and (c-i) is 7:1 to 1:3, preferably 4:1 to 1:2, particularly preferably 3:1 to 1:1.

In addition, in a further preferred embodiment of the process of the invention, the ratio of the weight of components (b-i) to (c-i) is 15:1 to 1:2, preferably 10:1 to 1:1, particularly preferably 7:1 to 3:1.

The mixture obtained from step (i) preferably has a water content of 0.01 to 4% by weight, preferably 0.1 to 2% by weight, in particular 0.2 to 1.5% by weight. The water content here is determined by means of the above-mentioned halogen moisture method.

In step (ii), the mixture obtained from step (i) is compacted. In the context of this invention, compacting is usually understood to mean the conversion of a powder mixture by applying pressure, preferably mechanical pressure, into compacted material, such as slugs or briquettes.

The compacting can be performed in conventional compacting apparatuses. The compacting is preferably carried out in a roll compacter, e.g. Polygran® (Gerteis). The rolling force is usually 1 to 50 kN/cm, preferably 2 to 30 kN/cm, more preferably 3 to 15 kN/cm. The gap width of the roll granulator is, for example, 0.8 to 6 mm, preferably 1.5 to 5.0 mm, more preferably 2.5 to 4.0 mm, especially 2.8 to 3.8 mm.

The compacting conditions are usually selected such that the intermediate of the invention is present in the form of a slug of compacted material, the density of the intermediate being 0.8 to 1.3 g/cm$^3$, preferably 0.85 to 1.20 g/cm$^3$, especially 0.90 to 1.15 g/cm$^3$. The figures relate to the apparent density.

In step (iii), the compacted material obtained in step (ii) is milled into granules. The milling in this context can usually be carried out with the aid of milling tools, such as counter-rotating toothed-roll crushers, sieves or mixers as described above. It is preferable to use sieves for this purpose, especially sieves with a mesh width of 0.1 to 5 mm, preferably 0.5 to 3 mm, more preferably 0.75 to 2 mm, especially 0.8 to 1.8 mm. Alternatively, mixers can also be used, such as asymmetric moved mixers.

In a preferred embodiment, the milling conditions are selected such that the resulting particles (granules) have a particle size (D50) of 50 to 400 µm, more preferably 60 to 250 µm, even more preferably 90 to 200 µm, especially 110 to 180 µm.

The resulting intermediates can then be used for the preparation of an orodispersible tablet of the invention. As explained above, the present invention also relates in addition to a process for the preparation of an orodispersible tablet containing sildenafil base, comprising the steps of
(I) preparing an intermediate of the invention,
(II) mixing the intermediate with further pharmaceutical excipients, and
(III) compressing the mixture from step (II) into an orodispersible tablet.

The term "orodispersible tablet" is understood in the context of this invention to mean an orally dispersible tablet. Hence, an orodispersible tablet is a tablet that disintegrates orally, in the buccal cavity. During or after disintegration, the components of the tablet of the invention may not be dissolved at all, or may be partially or completely dissolved by saliva. The orodispersible tablet is usually an uncoated tablet, i.e. it is not coated or film-coated. In particular, the orodispersible tablet is not a tablet coated with a polymer that is insoluble in saliva, as is described in U.S. Pat. No. 6,221,402 B1.

According to Ph. Eur. 6.0, orodispersible tablets must disintegrate within 3 minutes. In the context of this invention, it is preferable that the orodispersible tablets of the invention should have a disintegration time of less than 100 seconds, more preferably less than 50 seconds, particularly preferably less than 30 seconds, in particular less than 25 seconds, in the mouth.

The disintegration time is determined in accordance with Ph. Eur. 6.0, section 2.9.1 Test A. Water is preferably used as the test liquid. When in the context of this application reference is made to the average disintegration time, this means the average of the disintegration times determined for 6 tablets.

The orodispersible tablets of the invention usually contain sildenafil base in a mass of 15 to 250 mg, more preferably 20 to 150 mg. In particular, they contain 25 mg, 50 mg or 100 mg of sildenafil base.

The orodispersible tablets of the invention usually have a total weight of less than 500 mg, more preferably less than 350 mg, in particular less than 250 mg. The orodispersible tablets of the invention usually have a weight of 35 mg, preferably 50 mg or more, in particular more than 60 mg.

In a preferred embodiment, the orodispersible tablets of the invention have a proportion of sildenafil base of 45 to 70% by weight, preferably 50 to 65% by weight, more preferably 51 to 60% by weight, based on the total weight of the orodispersible tablet.

With a content of active agent of 20 to 30 mg, the orodispersible tablets of the invention usually have a total weight of less than 200 mg, more preferably less than 150 mg, in particular less than 100 mg. When the content of active agent is 20 to 30 mg, the orodispersible tablets of the invention usually have a weight of more than 35 mg, preferably 50 mg or more, in particular more than 60 mg.

With a content of active agent of more than 30 mg and less than 70 mg, the orodispersible tablets of the invention usually have a total weight of less than 300 mg, more preferably less than 150 mg, in particular less than 120 mg. The orodispersible tablets of the invention usually have a weight of more than 60 mg, preferably 80 mg or more, in particular more than 85 mg.

With a content of active agent of 70 mg to 150 mg, the orodispersible tablets of the invention usually have a total weight of less than 500 mg, more preferably less than 350 mg, in particular less than 300 mg.

The weight ratio of active agent to excipients in the orodispersible tablets of the invention is usually 5:1 to 1:3, preferably 3:1 to 1:2, especially 2.0:1 to 1:1.5.

The orodispersible tablets of the invention are therefore clearly distinct from "chewable tablets", since the latter usually have a higher weight (approx. 1.5 to 3 g) and a longer disintegration time.

The orodispersible tablets of the invention usually have a hardness 25 to 120 N, preferably 30 to 90 N, more preferably 35 to 60 N. The hardness is usually determined in accordance with Ph. Eur. 6.0, section 2.9.8. When in the context of this application reference is made to the average hardness, this means the average of the hardness determined for 10 tablets.

In addition, the resulting tablets preferably have a friability of less than 3%, particularly preferably less than 1%, especially less than 0.5%. The friability is determined in an apparatus in accordance with Ph. Eur. 6.0, section 2.9.7, where 20 tablets are tested for 10 minutes at 25 r.p.m. and 25° C.

In a preferred embodiment, the orodispersible tablets of the invention preferably have a water content of <4.5% by weight, preferably 0.01 to 3.0% by weight, in particular 0.1 to 1.5% by weight, determined with the HR83 halogen moisture apparatus explained above.

In step (I) of the process of the invention for the preparation of an orodispersible tablet, the intermediate of the invention is prepared as described above. The intermediate of the invention then forms the "inner phase" in the process of the invention for the preparation of the orodispersible tablet. The components of the inner phase are also referred to as "intragranular components".

In step (II) of the process of the invention for the preparation of an orodispersible tablet, the intermediate of the invention is mixed with further pharmaceutical excipients. In the process of the invention for the preparation of the orodispersible tablet, the excipients added in step (II) then form the "outer phase". The components of the outer phase are also referred to as "extragranular components".

Further pharmaceutical excipients in this context can usually be any standard pharmaceutical excipients for the preparation of a tablet, especially an orodispersible tablet.

The term "mixing" is understood here in the context of the invention as defined above.

In a preferred embodiment, the pharmaceutical excipients used in step (II) are the components (b-ii) wicking agent, (c-ii) disintegrant, optionally (d-ii) glidant and optionally (e-ii) lubricant. The designations (b-ii), (c-ii), (d-ii) and (e-ii) indicate that these excipients are added to form the outer phase.

In this context, the components wicking agent (b-ii), disintegrant (c-ii) and glidant (d-ii) are understood as defined above for the preparation of the intermediate of the invention.

Lubricants (e-ii) are generally substances which are used in order to reduce sliding friction. In particular, the intention is to reduce the sliding friction found during tablet pressing between the punches moving up and down in the die and the die wall, on the one hand, and between the edge of the tablet and the die wall, on the other hand. Suitable lubricants are, for example, stearic acid, adipic acid, sodium stearyl fumarate (e.g. Pruv®), magnesium stearate and/or calcium stearate. Stearyl fumarate (e.g. PRUV®) is preferably used as a lubricant in the context of the invention sodium. Magnesium stearate is particularly preferably used as a lubricant, especially with batch sizes of more than 5 kg.

Component (b-ii) wicking agent is usually employed in step (II) in an amount of 1 to 10% by weight, more preferably 2 to 8% by weight, in particular 3 to 7% by weight, based on the total weight of the orodispersible tablet.

Component (c-ii) disintegrant is usually employed in step (II) in an amount of 1 to 10% by weight, more preferably 2 to 8% by weight, in particular 3 to 6% by weight, based on the total weight of the orodispersible tablet.

Component (d-ii) glidant is usually employed in step (II) in an amount of 0 to 10% by weight, more preferably 0.1 to 5% by weight, in particular 0.5 to 3% by weight, based on the total weight of the orodispersible tablet.

Component (e-ii) lubricant is usually employed in step (II) in an amount of 0 to 10% by weight, more preferably 0.1 to 7% by weight, in particular 0.5 to 5% by weight, based on the total weight of the orodispersible tablet.

In the process of the invention, the weight ratio of intragranular wicking agent (b-i) to extragranular wicking agent (b-ii) is usually from 10:1 to 1:1, preferably 5:1 to 2:1. In addition, the weight ratio of intragranular disintegrant (c-i) to extragranular disintegrant (c-ii) is usually from 5:1 to 1:5, preferably 2:1 to 1:2. Furthermore, the weight ratio of intragranular glidant (d-i) to extragranular glidant (d-ii) is usually from 5:1 to 1:5, preferably 2:1 to 1:2.

In a preferred embodiment of the process of the invention for the preparation of the intermediate or in the process of the invention for the preparation the orodispersible tablet, microcrystalline cellulose is used as the wicking agent (b-i) and/or (b-ii), and/or crospovidone is used as the disintegrant (c-i) and/or (c-ii).

Anti-stick agents may optionally be used as further pharmaceutical excipients. "Anti-stick agents" are usually understood to mean substances which reduce agglomeration in the core bed. Examples are talcum, silica gel, polyethylene glycol (preferably with 2,000 to 10,000 g/mol weight-average molecular weight) and/or glycerol monostearate. Talcum is preferably used. Anti-stick agents are usually employed in an amount of 0 to 5% by weight, preferably 0.1 to 2% by weight, based on the total weight of the orodispersible tablet.

Fillers can likewise be used as further pharmaceutical excipients. Fillers are, for example, calcium phosphates such as calcium hydrogen orthophosphate, especially in the form of the dihydrate, calcium carbonate, magnesium carbonate, magnesium oxide, and/or calcium sulphate. The orodispersible tablet of the invention may contain fillers in the inner and/or outer phase.

Furthermore, sweeteners and/or flavourings can be used as further excipients. Sweeteners and/or flavourings may be contained both in the inner and in the outer phase.

It is preferable to use sweeteners which have a sweetening power of 0.2 to 13,000, preferably >1 to 4,000, in particular 10 to 1,000, based on the sweetening power of cane sugar (=1.0).

Examples are milk sugar (0.27-0.3), glycerine (0.5-0.8), D-glucose (0.5-0.6), maltose (0.6), galactose (0.6), invert sugar (0.8-0.9), cane sugar (1.0), xylitol (1.0), D-fructose (1.0-1.5), sodium cyclamate (30), D-tryptophan (35), chloroform (40), glycyrrhizin (50), acesulphame (130), aspartame (180-200), dulcin (200), Suosan® (350), saccharine (sodium salt) (400-500), saccharine (ammonium salt) (600), 1-bromo-5-nitroaniline (700), naringine dihydrochalcone (1,000-1,500), thaumatin, monellin (peptides) (3,000), P-4000, n-propoxyp-2-amino-4-nitrobenzene (4,000), alitame (3,000) and/or neotame (13,000). The numerical value in brackets shows the sweetening power based on crude sugar. Thaumatin and/or neohesperidin DC can likewise be used.

In the orodispersible tablet of the invention, sweeteners are usually employed in an amount of 0.1 to 5% by weight, more preferably 0.5 to 4% by weight, in particular 0.1 to 3% by weight, based on the total weight of the orodispersible tablet.

The orodispersible tablets of the invention may also contain one or more flavourings. In the context of this application, the term "flavourings" is to be understood as defined in Council Directive 88/388/EEC of 22 Jun. 1988.

In step (III) of the process of the invention, the mixture obtained from step (II) is compressed into an orodispersible tablet. "Compressing" here is usually understood to mean converting a mixture of substances into a dosage form, preferably an orodispersible tablet, with the aid of a tableting machine by applying pressure.

For the compressing step (III), substantially the intermediate of the invention in granulated form with further pharmaceutical excipients as described below is used.

The tableting conditions are preferably selected such that the resulting tablets have a ratio of tablet height to weight of 0.01 to 0.1 mm/mg, particularly preferably 0.03 to 0.06 mm/mg.

Conventional tableting machines used in the production of tablets can be used. Rotary presses or eccentric presses are preferably used. By applying a suitable compaction force, the problems explained at the beginning can be solved particularly advantageously, especially with regard to the physical properties (e.g. hardness and friability) of the tablets to be prepared. In the case of rotary tableting presses, a compressive force of 0.003 to 0.40 kN/mm, preferably 0.006 to 0.1 kN/mm, is usually applied. The compressive force is applied here as a force in kilonewtons per $mm^2$ tablet surface area, preferably the perpendicularly projected tablet surface area.

In the case of eccentric tableting presses, a compressive force of 0.01 to 0.07 kN/mm with a Korsch® EK0 or Korsch® XP1 is usually applied.

In a preferred embodiment, the process of the invention for the preparation of the intermediate and the process of the invention for the preparation of the orodispersible tablet is carried out in the absence of solvents. Solvents in this context usually mean water and/or organic solvents, such as methanol, ethanol and isopropanol, for example.

As already explained, the present invention relates to an intermediate which is obtainable by the process of the invention described above. In addition, the present invention relates to an orodispersible tablet which is obtainable by the process of the invention described above.

Hence, the present invention relates to an orodispersible tablet which is preferably obtainable by the process of the invention, containing 45 to 70% by weight, preferably 50 to 60% by weight, sildenafil base, 10 to 35% by weight, preferably 20 to 30% by weight, wicking agent, in particular microcrystalline cellulose, 5 to 20% by weight, preferably 7 to 15% by weight disintegrant, in particular crospovidone and/or starches or starch derivatives, in particular sodium carboxymethyl starch, 0 to 5% by weight, preferably 1 to 3% by weight, glidant, in particular silicon dioxide, 0 to 10% by weight, preferably 1 to 5% by weight, lubricant, in particular sodium stearyl fumarate.

In a preferred embodiment of the orodispersible tablet of the invention, the ratio of volume in $cm^3$ to mass of sildenafil base in mg is from 1 to 5 $cm^3$/mg, preferably 2 to 4 $cm^3$/mg.

Finally, a further subject matter of the present invention is the use of sildenafil, in particular sildenafil base, in particulate form, wherein the D50 value of the particle size distribution is 10 to 55 μm and the D90 value of the particle size distribution is 60 to 250 μm, for the preparation of an orodispersible tablet with a hardness of 30 to 90 N, preferably 40 to 80 N, and a friability of less than 1%, preferably 0.01 to 0.5%, particularly preferably 0.05 to 0.3%.

The present invention thus makes it possible to prepare an orodispersible tablet with an advantageously high sildenafil content, wherein the orodispersible tablet can be free of saccharide. Despite the high sildenafil content, the tablet of the invention produces an advantageous feeling in the patient's mouth. The invention further provides a technically advantageous (e.g. inexpensive) production process which, especially also in the case of larger batches, leads to an advantageous content uniformity in the resulting tablets.

The invention will now be illustrated with reference to the following examples.

EXAMPLES

Preparation

The following production process was used to prepare orodispersible tablets according to Examples 1 to 3.

Substances 1 to 4 were sieved using a 1 mm sieve and filled into a steel drum. Using a Rhoenrad asymmetric moved mixer, the substances were mixed for 10 minutes. After that, the mixture was granulated with a dry compactor (Gerteis Polygran®). Substances 5 to 10 were sieved using a 1 mm sieve. Substances 5 to 8 were mixed with the granules.

The mixture obtained in this way was then mixed for 10 minutes using an asymmetric moved mixer. Talcum and colloidal silicon dioxide were added and mixed for 5 minutes. The glidant sodium stearyl fumarate was then sieved in, using a 0.8 mm sieve. After the glidant had been added to the mixture, the mixture obtained was mixed for 2 minutes. The mixture ready for tableting was compressed into tablets using different compression pressures (Ex. 1: 0.025 kN/mm, Ex. 2a: 0.045 kN/mm, Ex. 2b: 0.02 kN/mm, Ex. 3: 0.02 kN/mm) with a rotary press.

Example 1

TABLE 1

Composition for the preparation of an orodispersible tablet containing sildenafil base 100 mg

| Starch | | 100 mg | |
|---|---|---|---|
| | Name | (mg/dose) | % |
| | Inner phase: | | |
| 1 | sildenafil base | 100.00 | 55.87 |
| 2 | cellulose, microcrystalline PH 112 | 40.00 | 22.35 |
| 3 | crospovidone | 6.00 | 3.35 |
| 4 | colloidal silicon dioxide | 2.00 | 1.12 |
| | Outer phase: | | |
| 5 | cellulose, microcrystalline PH 112 | 9.60 | 5.36 |
| 6 | crospovidone | 9.00 | 5.03 |
| 7 | natural mint aroma | 2.40 | 1.34 |
| 8 | Aspartame ® | 1.00 | 0.56 |
| 9 | talcum | 2.00 | 1.12 |
| 10 | colloidal silicon dioxide | 2.00 | 1.12 |
| 11 | sodium stearyl fumarate | 5.00 | 2.79 |
| | Total: | 179.0 | 100.0 |

Examples 2a and 2b

TABLE 2

Composition for the preparation of an orodispersible tablet containing sildenafil base 50/100 mg

| Starch | | 50 mg | 100 mg | |
|---|---|---|---|---|
| | Name | (mg/dose) | (mg/dose) | % |
| | Inner phase: | | | |
| 1 | sildenafil base | 50.00 | 100.00 | 54.95 |
| 2 | cellulose, microcrystalline PH 112 | 19.00 | 38.00 | 20.88 |
| 3 | crospovidone | 4.00 | 8.00 | 4.40 |
| 4 | colloidal silicon dioxide | 1.00 | 2.00 | 1.10 |
| | Outer phase: | | | |
| 5 | cellulose, microcrystalline PH 112 | 5.40 | 10.80 | 5.93 |
| 6 | crospovidone | 4.50 | 9.00 | 4.95 |
| 7 | natural mint aroma | 1.50 | 3.00 | 1.65 |
| 8 | Aspartame ® | 0.60 | 1.20 | 0.66 |
| 9 | talcum | 1.00 | 2.00 | 1.10 |
| 10 | colloidal silicon dioxide | 1.00 | 2.00 | 1.10 |
| 11 | sodium stearyl fumarate | 3.00 | 6.00 | 3.30 |
| | Total: | 91.0 | 182.0 | 100.0 |

Example 3

TABLE 3

Composition for the preparation of an orodispersible tablet containing sildenafil base 100 mg

| Starch | | 100 mg |
|---|---|---|
| | Name | (mg/dose) |
| | Inner phase: | |
| 1 | sildenafil base | 100.00 |
| 2 | cellulose, microcrystalline PH 112 | 40.00 |
| 3 | crospovidone | 6.00 |
| 4 | colloidal silicon dioxide | 2.00 |
| | Outer phase: | |
| 5 | cellulose, microcrystalline PH 112 | 10.80 |
| 6 | crospovidone | 9.00 |
| 7 | natural mint aroma | 3.00 |
| 8 | Aspartame ® | 1.20 |
| 9 | talcum | 2.00 |
| 10 | colloidal silicon dioxide | 2.00 |
| 11 | sodium stearyl fumarate | 8.00 |
| | Total | 184.0 |

Examples 4a and 4b

In order to prepare orodispersible tablets in accordance with Example 4, substances 1 to 5 were sieved using a 1 mm sieve and filled into a steel drum. Using a Rhoenrad asymmetric moved mixer, the substances were mixed for 10 minutes. After that, the mixture was granulated with a dry compactor (Gerteis Polygran®). Substances 6 to 11 were sieved using a 1 mm sieve and added to the granules. The mixture obtained in this way was then mixed for 10 minutes using an asymmetric moved mixer. Talcum (12) and colloidal silicon dioxide (13) were added and mixed for 5 minutes. The glidant sodium stearyl fumarate (14) was then sieved in, using a 0.8 mm sieve. After the glidant had been added to the mixture, the mixture obtained was mixed for 2 minutes. The mixture ready for tableting was compressed into tablets using different compression pressures (Ex. 4a: 0.02 kN/mm, Ex. 4b: 0.03 kN/mm) with a rotary press.

TABLE 4

Composition for the preparation of an orodispersible tablet containing sildenafil base 50/100 mg

|   | Starch Name | 50 mg (mg/dose) | 100 mg (mg/dose) |
|---|---|---|---|
|   | Dry granules: |   |   |
| 1 | sildenafil base | 50.00 | 100.00 |
| 2 | microcrystalline cellulose | 30.00 | 60.00 |
| 3 | dibasic calcium phosphate | 16.00 | 32.00 |
| 4 | sodium starch glycolate | 2.00 | 4.00 |
| 5 | colloidal silicon dioxide | 1.00 | 2.00 |
|   | Outer phase: |   |   |
| 6 | sodium starch glycolate | 3.00 | 6.00 |
| 7 | starch | 15.65 | 31.30 |
| 8 | natural mint aroma | 0.30 | 0.60 |
| 9 | menthol aroma | 0.45 | 0.90 |
| 10 | lemon aroma | 1.20 | 2.40 |
| 11 | saccharine | 0.10 | 0.20 |
| 12 | talcum | 1.00 | 2.00 |
| 13 | colloidal silicon oxide | 2.00 | 4.00 |
| 14 | sodium stearyl fumarate | 3.75 | 7.50 |

Evaluation

In Examples 1 to 3, it was possible to achieve concentrations of active agent of more than 50% by weight, based on the total weight of the orodispersible tablet. Even with an amount of active agent of 100 mg, the total weight of the orodispersible tablet was well under 200 mg.

Friability

The friability for orodispersible tablets according to Example 1 was 0.25%. The friability for orodispersible tablets according to Example 2 with the 50 mg strength of active agent (Ex. 2a) was 0.05% and for orodispersible tablets with the 100 mg strength of active agent (Ex. 2b) it was 0.15%. Orodispersible tablets according to Example 3 exhibited a friability of 0.25%.

Hardness

The average hardness for orodispersible tablets according to Example 1 was 70 N. The average hardness for orodispersible tablets according to Example 2 with the 50 mg strength of active agent (Example 2a) was 50 N and for orodispersible tablets with the 100 mg strength of active agent (Example 2b) it was 80 N. In addition, the average hardness for orodispersible tablets according to Example 3 was 70 N.

Disintegration Time

The average disintegration times were determined here immediately after the orodispersible tablets had been produced (time $T_0$.), after the orodispersible tablets had been stored for 7 days (time $T_7$) and after they had been stored for 25 days (time $T_{25}$) at 25° C. and 55% relative humidity.

Time $T_0$

The average disintegration time for the orodispersible tablets prepared in accordance with Example 1 at time $T_0$ was 20 sec. The average disintegration time for the orodispersible tablets prepared in accordance with Example 2 with a strength of active agent of 50 mg at time $T_0$ was 10 sec, and that for the orodispersible tablets prepared in accordance with Example 2 with a strength of active agent of 100 mg at time $T_0$ was 35 sec. In addition, the average disintegration time for the orodispersible tablets prepared in accordance with Example 3 at time $T_0$ was 25 sec.

Times $T_7$ and $T_{25}$

It has been found that the average disintegration time of the orodispersible tablets of the invention did not undesirably increase significantly even after the relevant storage time.

Taste/Feeling in the Mouth

Since taste sensations and sensations associated with the feeling in the mouth can vary from one individual to another, 5 test candidates were used to test the taste and the feeling in the mouth, and the average scores for taste and feeling in the mouth were determined immediately after the orodispersible tablets prepared in accordance with Examples 1 to 3 were taken. The test for taste and feeling in the mouth was performed 1 hour after the last meal. The test candidates were all male and non-smokers. The test room was neutral in odour, the temperature was 20° C. The stimulated sensations were assessed and the test candidates were trained in accordance with DIN 10950.

The test candidates were able to score their sentiments with regard to the feeling in the mouth on a scale from 1 to 3. The different scores of 1 to 3 were defined as follows: (1) "good feeling in the mouth", (2) "medium feeling in the mouth", (3) "bad feeling in the mouth". With regard to the feeling in the mouth, the vast majority of the test candidates awarded a score of "good feeling in the mouth" to the orodispersible tablets according to Examples 1 to 3.

The invention claimed is:

1. An orodispersible tablet comprising:
   45-70 wt % sildenafil base, wherein the particle size distribution (D50) of the sildenafil base is 1-25 μm;
   10-35 wt % microcrystalline cellulose; and
   5-20 wt % of a disintegrant, wherein the disintegrant is selected from the group consisting of crospovidone, sodium starch glycolate, and combinations thereof.

2. The orodispersible tablet of claim 1, further comprising colloidal silicon dioxide.

3. The orodispersible tablet of claim 2, wherein the concentration of colloidal silicon dioxide is 1-5% by weight of the orodispersible tablet.

4. The orodispersible tablet of claim 1, further comprising a lubricant selected from the group consisting of sodium stearyl fumarate and magnesium stearate.

5. The orodispersible tablet of claim 4, wherein the lubricant is sodium stearyl fumarate.

6. The orodispersible tablet of claim 5, wherein the concentration of sodium stearyl fumarate is 1-5% by weight of the orodispersible tablet.

7. The orodispersible tablet of claim 1, wherein the microcrystalline cellulose has a weight-average molecular weight of 10,000-70,000 g/mol.

8. The orodispersible tablet of claim 1, wherein the microcrystalline cellulose has a weight-average molecular weight of 25,000-45,000 g/mol.

9. The orodispersible tablet of claim 1, wherein the microcrystalline cellulose has a weight-average molecular weight of 30,000-40,000 g/mol.

10. An orodispersible tablet comprising:
    45-70 wt % sildenafil base, wherein the particle size distribution (D50) of the sildenafil base is 1-25 μm;
    20-35 wt % microcrystalline cellulose; and 5-20 wt % of a disintegrant, wherein the disintegrant is selected from the group consisting of crospovidone, sodium starch glycolate, and combinations thereof; and
    wherein the orodispersible tablet has a hardness of 30-90 N and a friability of 0.01-0.5%.

11. The orodispersible tablet of claim 10, wherein the concentration of sildenafil base is 50-70% by weight of the orodispersible tablet.

12. The orodispersible tablet of claim 10, wherein the concentration of sildenafil base is 50-60% by weight of the orodispersible tablet.

13. The orodispersible tablet of claim 10, wherein the concentration of microcrystalline cellulose is 20-30% by weight of the orodispersible tablet.

14. The orodispersible tablet of claim 11, wherein the concentration of microcrystalline cellulose is 20-30% by weight of the orodispersible tablet.

15. The orodispersible tablet of claim 12, wherein the concentration of microcrystalline cellulose is 20-30% by weight of the orodispersible tablet.

16. The orodispersible tablet of claim 14, wherein the hardness is 35-60 N.

17. The orodispersible tablet of claim 10, wherein the microcrystalline cellulose has a weight-average molecular weight of 30,000-40,000 g/mol.

18. The orodispersible tablet of claim 15, wherein the microcrystalline cellulose has a weight-average molecular weight of 30,000-40,000 g/mol.

19. The orodispersible tablet of claim 18, wherein the hardness is 35-60 N.

\* \* \* \* \*